United States Patent
Van Den Tillaart et al.

(10) Patent No.: US 9,505,712 B2
(45) Date of Patent: Nov. 29, 2016

(54) METHOD AND APPARATUS FOR THE PRODUCTION OF UREA FROM AMMONIA AND CARBON DIOXIDE

(71) Applicant: STAMICARBON B.V., Sittard (NL)

(72) Inventors: Johan Albert Arno Van Den Tillaart, Sittard (NL); Jozef Hubert Meessen, Sittard (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 14/398,425

(22) PCT Filed: May 2, 2013

(86) PCT No.: PCT/NL2013/050330
§ 371 (c)(1),
(2) Date: Oct. 31, 2014

(87) PCT Pub. No.: WO2013/165246
PCT Pub. Date: Nov. 7, 2013

(65) Prior Publication Data
US 2015/0119603 A1    Apr. 30, 2015

(30) Foreign Application Priority Data
May 3, 2012   (EP) .................................... 12166579

(51) Int. Cl.
C07C 273/04   (2006.01)
B01J 10/00    (2006.01)
B01J 19/00    (2006.01)

(52) U.S. Cl.
CPC ............ C07C 273/04 (2013.01); B01J 10/00 (2013.01); B01J 19/0013 (2013.01); *B01J 2219/00051* (2013.01); *Y02P 20/142* (2015.11)

(58) Field of Classification Search
CPC .................. B01J 10/00; B01J 19/0013; B01J 2219/00051; C07C 273/04

USPC ................................... 564/70; 422/198, 600
See application file for complete search history.

(56) References Cited

U.S. PATENT DOCUMENTS 4,866,207 A   9/1989   Jonckers et al.
5,767,313 A   6/1998   Jonckers
(Continued)

FOREIGN PATENT DOCUMENTS

EP   0 155 735        9/1985
EP   0266840 A1   *   11/1987
(Continued)

OTHER PUBLICATIONS

Billet ("Evaporation" Ullmann's Encyclopedia of Industrial Chemistry, published online Jun. 5, 2000, DOI: 10.1002/14356007.b03_03, p. 1-36).*
(Continued)

*Primary Examiner* — Jafar Parsa
*Assistant Examiner* — Amy C Bonaparte
(74) *Attorney, Agent, or Firm* — Morrison & Foerster LLP

(57) ABSTRACT

Method for the production of urea from ammonia and carbon dioxide in a urea plant containing a high-pressure synthesis section with a horizontal pool condenser, wherein the method comprises exchanging heat from a high pressure process medium received in a shell section of the pool condenser to a medium pressure urea containing solution received in a first heat exchanging section provided in the pool condenser to at least decompose ammonium carbamate into $NH_3$ and $CO_2$, wherein the method further comprises exchanging heat from the high pressure process medium to a low pressure steam condensate received in a second heat exchanging section provided in the pool condenser to produce low pressure steam. The invention also relates to an apparatus for the production of urea from ammonia and carbon dioxide.

7 Claims, 1 Drawing Sheet

(56) References Cited

U.S. PATENT DOCUMENTS 6,518,457 B1 * 2/2003 Sakata .................. C07C 273/04
564/67
7,582,795 B2 9/2009 Kojima

FOREIGN PATENT DOCUMENTS

| EP | 0417830 | 3/1991 |
| EP | 1 279 663 | 1/2003 |
| JP | 63-126857 | 5/1988 |
| JP | 2003-104949 | 4/2003 |
| WO | WO-02/090323 | 11/2002 |
| WO | WO-03/064379 | 8/2003 |
| WO | WO-2006/118071 | 11/2006 |
| WO | WO-2009/141344 | 11/2009 |
| WO | WO-2013/165247 | 11/2013 |

OTHER PUBLICATIONS

International Search Report for PCT/NL2013/050330, dated Jun. 13, 2013, 3 pages.

Meessen and Petersen, "Urea," in: Ullmann's Encyclopedia of Industrial Chemistry, Fifth, Completely Revised Edition, Elvers and Hawkins (eds.), VCH Verlagsgesellschaft mbH, Weinheim, Germany (1996) vol. A27, 48 pages.

Stamicarbon Urea Process, "A lower cost design for urea," Nitrogen (1996) 222:29-31.

* cited by examiner

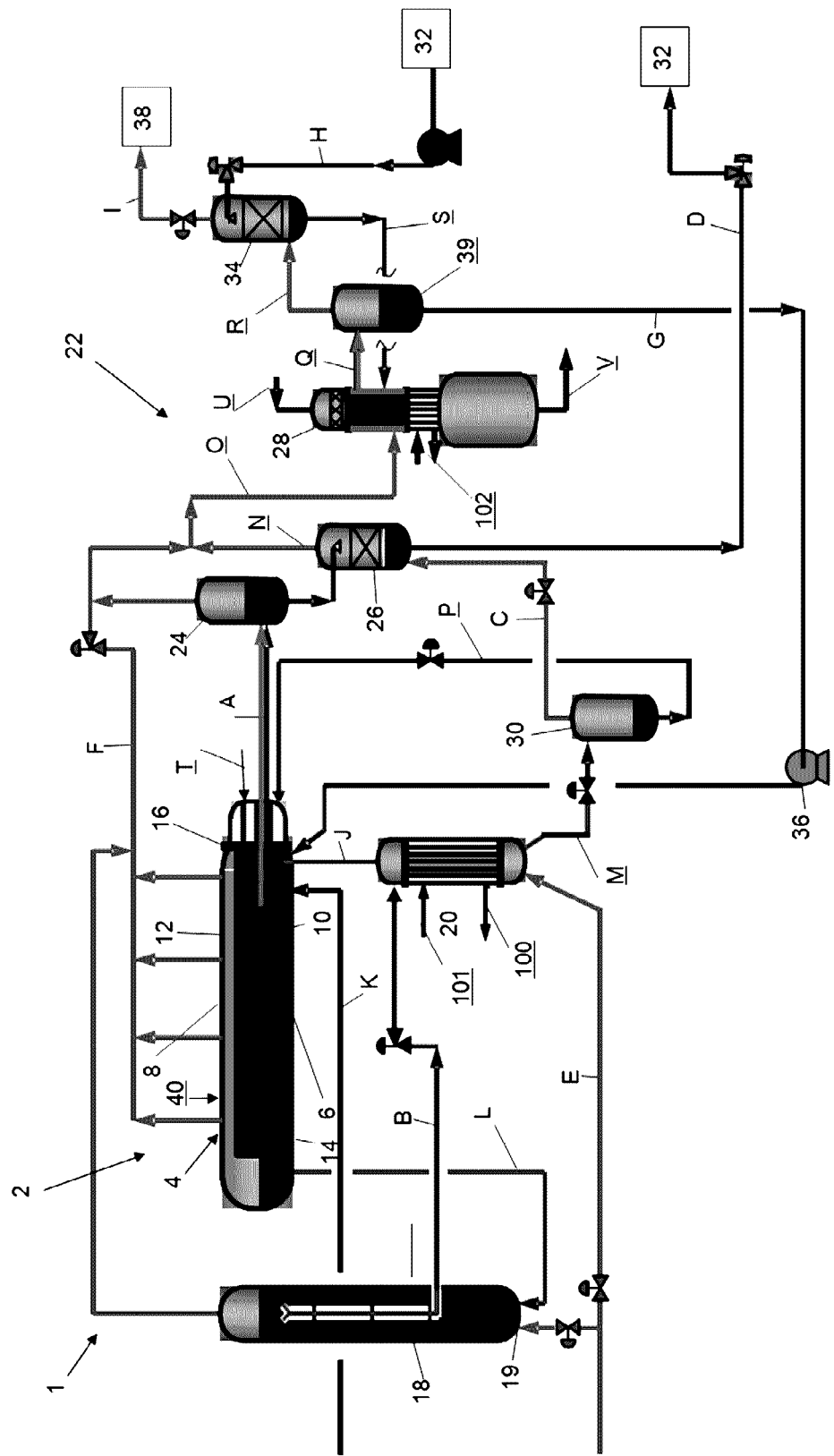

METHOD AND APPARATUS FOR THE PRODUCTION OF UREA FROM AMMONIA AND CARBON DIOXIDE

CROSS-REFERENCE TO RELATED APPLICATIONS

This application is the national phase of PCT application PCT/NL2013/050330 having an international filing date of 2 May 2013, which claims benefit of European patent application No. 12166579.8 filed 3 May 2012. The contents of the above patent applications are incorporated by reference herein in their entirety.

FIELD OF THE INVENTION

The present invention relates to the field of the production of urea from ammonia and carbon dioxide in a urea plant containing a high-pressure synthesis section.

BACKGROUND

Methods for the production of urea from ammonia and carbon dioxide in a urea plant are known. Such a method is for instance known from WO 2009/141344. The urea plant may comprise a high pressure stripper, a high pressure carbamate condenser and a pool condenser or a pool reactor. The method may be based on the so called n=2 heat integration concept in which heat supplied to the urea plant is used twice. The steam is used to heat the stripper. After recovering the heat in the high pressure carbamate condenser, pool condenser or pool reactor, the heat is re-used in the form of low pressure steam in other process sections in the urea plant, or is (partially) exported to users outside of the urea plant.

Due to the increasing costs of energy, thus also the increasing costs for producing urea from ammonia and carbon dioxide, improving the energy efficiency of urea plants is desirable.

Therefore, it is an object of the present invention to provide an improved method for the production of urea from ammonia and carbon dioxide in a urea plant. More in particular an object of the invention is to provide a method for the production of urea from ammonia and carbon dioxide in a urea plant that operates with reduced energy consumption.

SUMMARY OF THE INVENTION

According to one aspect of the invention a method for the production of urea from ammonia and carbon dioxide in a urea plant containing a high-pressure synthesis section with a horizontal pool condenser is provided. The method comprises exchanging heat from a high pressure process medium received in a shell section of the pool condenser to a medium pressure urea containing solution received in a first heat exchanging section provided in the pool condenser to at least decompose ammonium carbamate into $NH_3$ and $CO_2$. The method further comprises exchanging heat from the high pressure process medium to a low pressure steam condensate received in a second heat exchanging section provided in the pool condenser to produce low pressure steam.

With such a method, next to generating low pressure steam, carbamate is condensed to release heat which is used to decompose carbamate to $CO_2$ and $NH_3$. By integration of these two functions, the steam consumption of the urea plant used for the production of urea is decreased. Consequently, the energy consumption is lower than for instance used in afore described prior art method for the production of urea from ammonia and carbon dioxide. As a result energy efficiency is obtained and costs for the production of urea are reduced. It is noted that throughout this description a pool condenser is to be understood as a condenser in which the liquid phase is the continuous phase. Such a pool condenser may also be referred to as a submerged condenser.

It is further noted that throughout this description high pressure may typically be defined as a pressure above 100 bar (10 MPa), for instance 120 bar (12 MPa). Medium pressure may typically be defined as a pressure between 10-35 bar (1-3.5 MPa), for instance between 10-25 bar (1-2.5 MPa), intermediate pressure may typically be defined as a pressure between 20-100 bar (2.0-10 MPa), for instance between 25-100 bar (2.5-10 MPa) and low pressure may be typically defined as a pressure between 2-10 bar (0.2-1 MPa).

In order to integrate the above mentioned function, the pool condenser, according to another aspect of the invention, is a shell and tube heat exchanger, wherein the first and second heat exchanging sections each comprise a substantially U-shaped tube bundle. The shell and tube heat exchanger may be a submerged condenser that is placed horizontally. In different words, the shell and tube heat exchanger may comprise a vessel, which vessel is placed substantially horizontally, at least the central axis of the vessel extends substantially horizontally, to be able to perform the method according to the invention.

Said first and second U-shaped tube bundles extend from the tube sheet of the pool condenser at least partially through an inner space of the pool condenser. The second U-shaped tube bundle is configured for the generation of low pressure steam. The first U-shaped tube bundle is used for the heat integration with a medium pressure recirculation section. The first bundle, in use, is filled with a process medium from said medium pressure recirculation section. Thus, the first bundle is in contact with process medium on the tube side as well as the shell side thereof. Preferably, an oxidizing agent is added to the process for the production of urea to protect the materials of the different parts of the plant against corrosion. By doing so, an oxide skin is formed on the metal surfaces. The oxidizing agent may be oxygen, to be added in the form of air or as peroxide, or an oxygen-releasing compound. Besides, the parts that are in contact with the process medium may be made from an austenitic-ferritic duplex stainless steel grade, which has corrosion resistant properties. In that case, the use of an oxidizing agent may be reduced or even omitted in the process of the production of urea according to the invention.

Due to the integration of the above described functions, i.e. the condensation of carbamate and the release of heat that is subsequently used to decompose the carbamate into $NH_3$ and $CO_2$, without any intermediate heat transfer medium, the available temperature difference between both process sides enables the respective U-shaped tube bundles to be relatively small. This is advantageous with respect to the manufacturing costs of the apparatus for the production of urea with the method according to the invention.

In further elaboration of the invention, the high pressure process medium received in the shell section of the pool condenser is supplied to an after reactor provided downstream of the pool condenser. Preferably, fresh $CO_2$ is fed to the after reactor to provide heat for an endothermic urea reaction inside the after reactor to form a urea synthesis solution.

According to another aspect of the invention, the method further comprises feeding gas that is at least produced in the first heat exchanging section to a medium pressure condenser evaporator in which said gas is at least partially, and optionally completely, condensed. Before entering the first U-tube bundle of the pool condenser, the urea/carbamate solution is flashed to an intermediate pressure. The resulting liquid is further reduced to medium pressure and heated in the first U-tube bundle of the pool condenser, thereby thus effectively reusing the heat a first time, to decompose the liquid to $CO_2$ and $NH_3$. In the medium pressure condenser evaporator, at least the gas from the separator, provided downstream of the first U-shaped tube bundle, is condensed in the shell side of the evaporator. The heat of condensation liberated here is substantially used to evaporate water from an aqueous urea solution that is provided to the tube side of the medium pressure condenser evaporator. Thus, the heat is reused a second time to evaporate water from the urea water mixture on the tube side.

According to a further aspect of the invention, the water from a urea-water mixture may be evaporated under vacuum conditions in the medium pressure condenser evaporator.

Preferably, according to another aspect of the invention, the medium pressure condenser evaporator is a falling film evaporator. By designing the medium pressure condenser evaporator as a falling film evaporator, efficient counter current operation may be obtained. Somewhere along the condensation trajectory, for instance, halfway the condensation trajectory, carbamate coming from the low pressure recirculation section may be added via a medium pressure scrubber. By doing so, sufficient temperature difference may be maintained between the shell side and the tube side to obtain the efficient design of the medium pressure condenser evaporator.

The invention also relates to an apparatus for the production of urea from ammonia and carbon dioxide, preferably using a method according to any one of the preceding claims, wherein the apparatus comprises a high-pressure synthesis section with a horizontal pool condenser configured to receive a high pressure process medium at a shell side thereof, wherein the apparatus comprises a first heat exchanging section for exchanging heat from the high pressure process medium to a medium pressure urea solution received in said first heat exchanging section to decompose ammonium carbamate into $NH_3$ and $CO_2$, wherein the pool condenser comprises a second heat exchanging section for exchanging heat from the high pressure process medium to a low pressure steam condensate received in said second heat exchanging section to transfer said condensate into low pressure steam.

Such an apparatus provides similar effects and advantages as described with the method according to the invention.

The aforementioned and other features and advantages of the invention will be more fully understood from the following detailed description of certain embodiments of the invention, taken together with the accompanying drawings, which are meant to illustrate and not to limit the invention.

BRIEF DESCRIPTION OF THE DRAWINGS

FIG. 1 shows a schematic diagram of the method for production of urea from ammonia and carbon dioxide according to an embodiment of the invention.

DETAILED DESCRIPTION

Referring to FIG. 1, an example of a method for the production of urea from ammonia and carbon dioxide in a urea plant according to the invention is described with reference to the different elements of the apparatus 1 for producing urea. The urea plant comprises an apparatus 1 containing a high-pressure section 2 with a horizontal pool condenser 4, i.e. a so called shell and tube heat exchanger. The pool condenser 4 comprises a vessel, which in use, is placed substantially horizontally, with a first heat exchanging section 6 and a second heat exchanging section 8. In the shown embodiment, both heat exchanging sections 6, 8 comprise a substantially U-shaped tube bundle 10, 12. The first U-shaped tube bundle 10 is configured for condensation of carbamate and for subsequently decomposing of ammonium carbamate into $NH_3$ and $CO_2$ by means of the heat that is released during said condensation.

The second U-shaped tube bundle 12 is configured to produce low pressure steam. Both U-shaped bundles 10, 12 extend from the tube sheet 16 of the pool condenser 4 at least partly through an inner space defined by the shell 14 of the pool condenser 4.

The apparatus 1 may further comprise an after reactor, in the shown embodiment a vertical reactor 18, for the final reaction of the urea conversion. In another embodiment (not shown), the after reactor may be combined with the pool condenser. Preferably, the vertical reactor 18 is located at ground level. In the bottom section of the vertical reactor 18 an inlet 19 is provided for supplying fresh $CO_2$ to the reactor to enable the endothermic urea reaction. The apparatus 1 may also comprises a $CO_2$ stripper 20 and a medium pressure recirculation system 22. The latter system 22 may comprise a separator 24 arranged downstream of the first U-shaped tube bundle 10, a medium pressure rectifying column 26 and a medium pressure condenser evaporator 28.

The medium pressure condenser evaporator 28 may be a falling film evaporator to enable efficient counter current operation. It was found that an optimal operating pressure of the medium pressure section 22, of the shown embodiment, may be between 15-35 bar (1.5-3.5 MPa), more preferably between 20-30 bar (2-3 MPa). For instance, approximately 22.5 bar (2.25 MPa). In the low pressure section 32 of the apparatus 1 according to the shown embodiment of the invention, this optimal operating pressure may be between 2-7 bar (0.2-0.7 MPa), preferably between 4-6 bar (0.4-0.6 MPa). For instance, approximately 5.8 bar (0.58 MPa). Also the required pressure of steam on the shell of the stripper 20 may be significant lower as compared to the pressure of the prior art method that is described before. This may enable a further decrease of the total energy consumption since the pressure of the turbine extraction steam can be significant lowered.

The method according to the invention comprises feeding an amount of carbon dioxide to the vertical reactor 18. In the vertical reactor 18 a urea synthesis solution is formed which is supplied (arrow B) to the stripper 20. In the stripper 20, this solution is stripped by the addition of heat and with supplied carbon dioxide as a stripping gas (arrow E). Arrow B contains a valve symbol (angle blowdown valve). Hence, the stream is from unit 18 to unit 20. The same symbol is shown in arrow F (and arrows D and H). These symbols are similar to the valve symbols in, e.g., arrow E, except that they are at an angle. During stripping a mixed gas stream is obtained that is supplied to the pool condenser 4 (arrow J). Also fresh ammonia is supplied to the pool condenser 4 (arrow K). The urea solution that is formed in the vessel of the pool condenser 4 is supplied to the vertical reactor 18 (arrow L). Preferably, the synthesis pressure is kept at an operating level of between 125-175 bar (12.5-17.5 MPa), more preferably between 140-150 bar (14-15 MPa). For instance, approximately 144 bar (1.44 MPa).

The separator 24 is arranged downstream the first U-shaped tube bundle 10 and separates the gas phase and the liquid phase from said tube bundle 10. In the medium pressure recirculation system 22 also an intermediate flash tank 30 is provided that may supply $CO_2$ rich gas to the medium pressure rectifying column 26 (arrow C) to correct the $NH_3/CO_2$ ratio of the liquid from the first U-shaped tube bundle 10. The operating pressure used in the intermediate flash tank may be for instance between 20-80 (2-8 MPa), more preferably between 30 and 70 bar (3-7 MPa), even more preferably between 50-60 bar (5-6 MPa), for instance 55 bar (5.5 MPa). Subsequently, the liquid is discharged to the low pressure recirculation section 32 (arrow D).

The gas from the medium pressure rectifying column 26, the gas from the separator 24 and gas from the synthesis (arrow F) are combined and condensed in the shell side of the medium pressure condenser evaporator 28. Consequently, the heat is effectively reused a second time to evaporate water from the urea melt solution on the tube side. The medium pressure recirculation system 22 may further comprise a medium pressure scrubber 34. Somewhere along the condensation trajectory, for instance halfway said trajectory, carbamate coming from the low pressure recirculation section 32 is added to the medium pressure condenser evaporator 28 (shell-side) via the medium pressure scrubber 34. By doing so, sufficient temperature difference is maintained between the shell and tube side of the medium pressure condenser evaporator 28 resulting in an efficient heat exchanger design.

The concentrated carbamate solution coming from the shell side of the medium pressure condenser evaporator 28 is supplied to the pool condenser 4 (arrow G) using a high pressure carbamate pump 36. The uncondensed gases together with the inerts are scrubbed in the medium pressure scrubber 34 using the carbamate coming from the low pressure recirculation section 32 (arrow H). The resulting gas is supplied to the low pressure absorber 38 (arrow I).

In further explanation, of the non-limiting embodiment as shown in FIG. 1, urea containing solution (arrow M) from $CO_2$ stripper 20 is supplied to flash tank 30 as noted on page 6, line 28 and page 8, line 1. This flashing results in medium pressure urea containing solution, besides $CO_2$ rich gas C from the flash tank 30 as noted on page 8, line 1. The medium pressure urea containing solution comprises unreacted ammonium carbamate. In the exemplary embodiment shown, the medium pressure urea containing solution from flash tank 30 is supplied (arrow P) into the lower U-shaped tube bundle 10 in pool condenser 4 as noted above on page 6, lines 11-17. Hence, medium pressure urea containing solution is inside the U-shaped tube bundle, while high pressure process medium is in the pool condenser 4 in the shell section (40) at the shell side of the tubes of tube bundle 10. This allows for heat exchange between the urea-containing solution and the process medium while they are at different pressure. The process medium in the shell section is provided in part by the mixed gas stream J from stripper 20. In the shell section, ammonium carbamate is condensed from $CO_2$ and $NH_3$, thereby releasing heat of condensation. This heat is exchanged to the medium pressure urea-containing solution received inside the first U-shaped tube bundle, thereby increasing the temperature of that solution and causing decomposition of ammonium carbamate comprised in the medium pressure urea-containing solution into $NH_3$ and $CO_2$. Accordingly, a stream is obtained from U-shaped tube bundle 10 (labelled with arrow A in the FIGURE) comprising a liquid phase (urea solution) and a gas phase ($NH_3$ and $CO_2$) as noted on page 7, lines 28-30). The stream A is separated in separator 24 to give a liquid stream that is supplied to rectifying column 26 as noted on page 8, lines 2-3). The liquid stream is discharged as liquid stream D to a low pressure recirculation section 32. This urea containing liquid comprises the produced urea. Hence, the urea product is passed through the U-shaped tube bundle 10 in the embodiment shown. A stream of gas (arrow N) from rectifying column 26 is combined with gas stream (arrow F) to form a gas stream (arrow O) that is supplied to medium pressure condenser evaporator 28. A stream (arrow Q) from the shell section of medium pressure condenser evaporator 28 is supplied to a unit 39 separating carbamate solution (arrow G) from uncondensed gases (arrow R) as noted on page 8, lines 20-26. Uncondensed gases (arrow R) are supplied to medium pressure scrubber 34 to give a liquid stream (arrow S) and a gaseous stream (arrow I). Water stream (arrow U) is evaporated in a tube side of medium pressure condenser evaporator 28 and leaves as a stream (arrow V). Lines 100, 101 and 102 represent heat exchange.

Although an illustrative embodiment of the present invention has been described above, in part with reference to the accompanying drawing, it is to be understood that the invention is not limited to this embodiment. Variations to the disclosed embodiment can be understood and effected by those skilled in the art in practicing the claimed invention, from a study of the drawings, the disclosure, and the appended claims.

Reference throughout this specification to "one embodiment" or "an embodiment" means that a particular feature, structure or characteristic described in connection with the embodiment is included in at least one embodiment in the present invention. Thus, the appearances of the phrases "in one embodiment" or "in an embodiment" in various places throughout this specification are not necessarily all referring to the same embodiment. Furthermore, it is noted that particular features, structures or characteristics of one or more embodiments may be combines in any suitable manner to form new, not explicitly described embodiments.

The invention claimed is:

1. A method for the production of urea from ammonia and carbon dioxide in a urea plant containing a high-pressure synthesis section with a horizontal pool condenser comprising a shell section and first and second heat exchanging sections, wherein the method comprises
   exchanging heat from a high pressure process medium in which carbamate is formed from $NH_3$ and $CO_2$ in an exothermic reaction, which high pressure process medium is received in the shell section of the horizontal pool condenser
   with a medium pressure urea-containing solution that comprises ammonium carbamate, that is received in said first heat exchanging section to at least decompose in said first heat exchanging section ammonium carbamate into $NH_3$ and $CO_2$, and
   exchanging heat from the high pressure process medium contained in said shell section with a low pressure steam condensate received in said second heat exchanging section to produce low pressure steam.

2. The method of claim 1, wherein the pool condenser is a shell and tube heat exchanger, wherein the first and second heat exchanging sections each comprise a substantially U-shaped tube bundle.

3. The method of claim 1, wherein the high pressure process medium received in the shell section of the pool condenser is supplied to an after reactor provided downstream of the pool condenser.

4. The method of claim 3, wherein fresh $CO_2$ is fed to the after reactor to provide heat for an endothermic urea reaction inside the after reactor.

5. The method of claim 1, wherein the method further comprises feeding gas that is at least produced in the first heat exchanging section to a medium pressure condenser evaporator in which said gas is at least partially condensed.

6. The method of claim 5, wherein in the medium pressure condenser evaporator water from a urea-water mixture is evaporated at a tube side of the medium pressure condenser evaporator so as to occur under vacuum conditions.

7. The method of claim 5, wherein the medium pressure condenser evaporator comprises a falling film evaporator.

* * * * *